(12) United States Patent
Ghebre-Sellassie et al.

(10) Patent No.: US 6,499,984 B1
(45) Date of Patent: Dec. 31, 2002

(54) CONTINUOUS PRODUCTION OF PHARMACEUTICAL GRANULATION

(75) Inventors: Isaac Ghebre-Sellassie, Morris Plains, NJ (US); Matthew J. Mollan, Jr., Succasunna, NJ (US); Nitin Pathak, Succasunna, NJ (US); Mayur Lodaya, Succasunna, NJ (US); Mebrahtu Fessehaie, New York, NY (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/576,373

(22) Filed: May 22, 2000

(51) Int. Cl.⁷ .................. B28B 13/02; B29C 67/02; B02C 19/00
(52) U.S. Cl. ................. 425/135; 425/174.8 E; 425/202; 425/204; 425/222; 425/224; 264/117; 241/152.2; 241/260.1
(58) Field of Search ............... 425/135, 174.8 E, 425/202, 204, 224, 222; 264/117; 241/152.2, 260.1

(56) References Cited

U.S. PATENT DOCUMENTS 3,017,662 A  *  1/1962  Marsh ..................... 425/222
3,730,663 A  *  5/1973  Hare ...................... 425/222
3,743,461 A  *  7/1973  Williams .................. 425/222
5,047,246 A  *  9/1991  Gallian et al.
5,469,809 A  * 11/1995  Coleman
6,030,565 A  *  2/2000  Golan ..................... 264/117

FOREIGN PATENT DOCUMENTS

EP           304192 A1  *  2/1989   ............ B01J/02/16

* cited by examiner

Primary Examiner—Jan H. Silbaugh
Assistant Examiner—Adam R. Harris
(74) Attorney, Agent, or Firm—Charles W. Ashbrook; Matthew J. Russo (57) ABSTRACT

A single pass, continuous, automated system for producing a pharmaceutical granulation includes multiple feeders to feed powders and liquids, a twin screw processor to granulate, a radio frequency or microwave based drying apparatus to dry the granulation, and at least one mill to process the dried granulation to desired particle sizes. The system incorporates means for monitoring key process parameters on-line, all of which are controlled by a controller provided with feedback at each component of the system. The granulation produced can be compressed into a tablet or incorporated into a capsule, both having a uniform distribution of the active ingredient. The system produces product having consistent properties even when production is scaled up for manufacture of the tablet in commercial volume.

7 Claims, 7 Drawing Sheets

CONTINUOUS PRODUCTION OF PHARMACEUTICAL GRANULATION

FIELD OF INVENTION

The present invention relates to a method and apparatus for producing a pharmaceutical granulation product which is typically compressed into tablets or filled into hard gelatin capsules. More particularly, it pertains to a single-pass automated system and an apparatus for continuous production of a pharmaceutical granulation which incorporates wet granulation, drying, and milling.

BACKGROUND OF THE INVENTION

Granulation is a critical unit operation in the manufacture of solid oral dosage forms. Even with constant improvements in tableting equipment for automating production and increasing product output, powder granulations must still possess specific physical properties to ensure smooth operations in downstream processing. Thus, consistent product quality is often the most important motivation that guides advances in granulation techniques. Other significant goals are maintaining regulatory compliance, reducing cycle times, increasing process efficiency, and achieving production cost savings.

Advancements in wet granulation technology include high shear mixer granulators, single pot processing with a high shear mixer granulator and microwave drying, and a high shear granulator integrated with a fluid bed dryer, such as a semi-continuous multi cell apparatus. While these techniques provide some advantages over previously used granulation methods, there are specific shortcomings with each technique and, most importantly, none provide a true continuous granulation process starting with individual ingredients or a powder blend.

For example, in a single pot microwave based granulator using a high shear mixer, blending and agglomeration are accomplished by an impeller; while a chopper imparts high mechanical agitation to the blend of ingredients. Even though this granulator allows short processing time and the option of drying within the same equipment, the granulator is not efficient in granulating cohesive materials; it produces non-uniform shaped and sized granules; it degrades fragile granules; it allows uncontrolled granule growth; and it produces granules with low porosity.

In addition, Glatt GmbH (of Binzen Germany) has disclosed the use of a semi-continuous system (the "Glatt Multicell GMC") in which small batches of raw materials are conveyed in successive batches into a high shear, mixer-granulator which mixes and granulates the materials. The wet granulation is sequentially vacuum conveyed through a series of three fluid bed dryers for drying. Each unit operation occurs sequentially as the mini-batch moves through the system.

For drying ingredients during the manufacture of pharmaceutical products, conduction and convection have been the two most prevalent heating methods used. For drying pharmaceutical solids, use of convection is preferred to use of conduction because conductive heat transfer requires temperatures that would potentially result in product degradation. Nevertheless, in convective drying, either a high volume of air flow or long residence times are required to achieve the required reduction in moisture levels. In some instances, vacuum conditions are used to further enhance the removal of the evaporated moisture. The high volume of air flow or long residence times from convective drying can degrade or otherwise damage a pharmaceutical product produced therefrom. To a lesser degree, microwave energy has also been used, but only in batch mode. At present, no conventional drying systems provide a true single pass drying process with a first in-first out principle.

Therefore, there exists a need for a granulation process, a drying process, and a single pass, fully automated, continuous system which enables production of pharmaceutical granulation with consistent physical properties.

SUMMARY OF THE INVENTION

The present invention provides a single pass continuous, automated process for producing a granulation product, which can be further processed to make a solid oral dosage form, such as a tablet or capsule.

In one embodiment, the present invention comprises a twin screw wet granulator-chopper (TSWGC), to which active ingredient(s) and solid and liquid additives are fed, which mixes, granulates, and wet mills those components to form a granulation product.

In another embodiment, the present invention comprises a drying apparatus which dries granulation using dielectric energy, such as radio frequency energy, low frequency (conventional) microwave energy, or high frequency (millimeter wave) microwave energy, in a continuous, single pass mode, optionally incorporating a product isolation tunnel.

In a further embodiment, the present invention comprises integrated, automated process control of the components of the system such that key process parameters and product properties are monitored along the length of the system; for example, the moisture content of the granulation and the uniformity of the distribution of active ingredient(s) are monitored on-line, and feedback is provided to the individual components which adjusts conditions to achieve optimal parametric release of the product.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawings are the following figures.

DETAILED DESCRIPTION OF THE INVENTION

The present invention comprises an automated, single pass system, including process and apparatus, for continuous production of pharmaceutical granulation that can be further processed to make solid oral dosage forms. This system includes a twin screw wet granulator-chopper (TSWGC); a single pass drying apparatus which uses dielectric energy, such as radio frequency (RF), microwave energy, or both. These components produce a granulation having superior properties when incorporated into a pharmaceutical product. The TSWGC may be used in combination with the dielectric energy-based drying apparatus or, alternatively, it may be used separately with conventionally used components, such as a fluid bed or a continuous paddle dryer. In addition, the dielectric energy-based drying apparatus may be used with the TSWGC or, alternatively, it may be used separately with conventionally used components, such as a high shear granulator.

The TSWGC overcomes the limitations of conventional wet granulation equipment. The TSWGC comprises conveying, mixing, granulating and chopping elements to achieve distributive and, when desired, dispersive mixing. The design and alignment of the screw elements can be varied to process active ingredients and additives of varying bulk densities so that a homogeneous granulation product is produced. The TSWGC provides product densification and uniformity that exceeds the capabilities of a high shear granulator and, when used with the dielectric-based drying apparatus of the present invention, has drying speeds equivalent to or better than that of a fluid bed granulator/dryer.

The TSWGC differs from conventional extruders in several ways. The exit point is open-ended as opposed to a die plate in a conventional extruder; it has extended shafts that may optionally protrude out from the open end; and chopping elements are located at the exit end. It has one or more powder and liquid feeding zones, with a custom designed feeding zone for simultaneous feeding of liquid and powder. An additional feature of TSWGC is a shaft retainer seal, which prevents the forward motion of the screw shaft during operation.

The active ingredient(s) and additives (i.e., excipients, binders, plasticizers, etc.) are fed into the TSWGC such that: (1) solid ingredients are fed using multiple loss-in-weight type feeders which continuously monitor the weight of solid ingredients being fed; and (2) liquid ingredients are fed using multiple pumps combined with mass flow meters or loss-in-weight type feed tanks. The feed barrels can be modified for simultaneous feeding of liquids and powders.

The TSWGC mixes and granulates the active ingredient(s) and additives using a twin screw processor. The threads of the screw elements are arranged to optimize mixing and granulation to achieve the required granulate structure for the active ingredient(s) and additives being granulated. This arrangement enables wet milling within the TSWGC, which obviates the need for a separate wet milling step. The active ingredient(s) and additives are fed directly into the TSWGC. In addition, the arrangement of the conveying elements and the venting devices at the feed point remove entrapped air and maximize product throughput. The TSWGC utilizes liquids to heat and cool the granulation and to provide more uniformity in temperature and better temperature control at the temperatures used for granulation.

The wet granulation exits the twin screw processor through the open end as discrete granulation particles. The granulation particles are then leveled and deposited uniformly onto the belt of the drying unit using a load/leveling device. The drying unit uses dielectric energy, such as radio frequency or microwave energy, to remove moisture from the granulation in a one pass, continuous mechanism. Further, the drying unit is designed to have proper air flow for moisture removal, and the electrodes used in the drying unit are designed so that they may be offset and tilted, when required, such that moisture is removed while maintaining the granulation in the desired temperature range. Once dried, the granulation is transported to the milling component by a conveying system. At the milling component, the particle size of the dried granulation is reduced by an appropriate mill, such as a hammer mill, cone mill, fitz mill, pin mill, or other appropriate screening device.

The components of the system for producing the granulation product may be controlled by a master controller, which adjusts parameters in the system in response to production conditions measured at various points/components along the system. The parameters and conditions are measured on-line so that the system is continuous with each element of material produced having the same processing/shear history. For example, the moisture content of the granulation and the uniformity of the distribution of active ingredient(s) are monitored on-line, and feedback is provided to the individual components which allows adjustments of conditions. More specifically, the moisture content of the granulation product can be measured, for example, after it exits the TSWGC or after it is dried, and if that measurement is outside of the tolerated range (e.g., 0–10% after drying), conditions are adjusted to achieve optimal parametric release of the product.

The composition of the resulting granulation is more homogeneous and uniform than conventionally produced granulation. In addition, the transfer of the present invention's technology for commercial production is quicker than if using conventional, non-continuous processes because fewer scale-up steps are involved in the system of the present invention.

Figure 1:
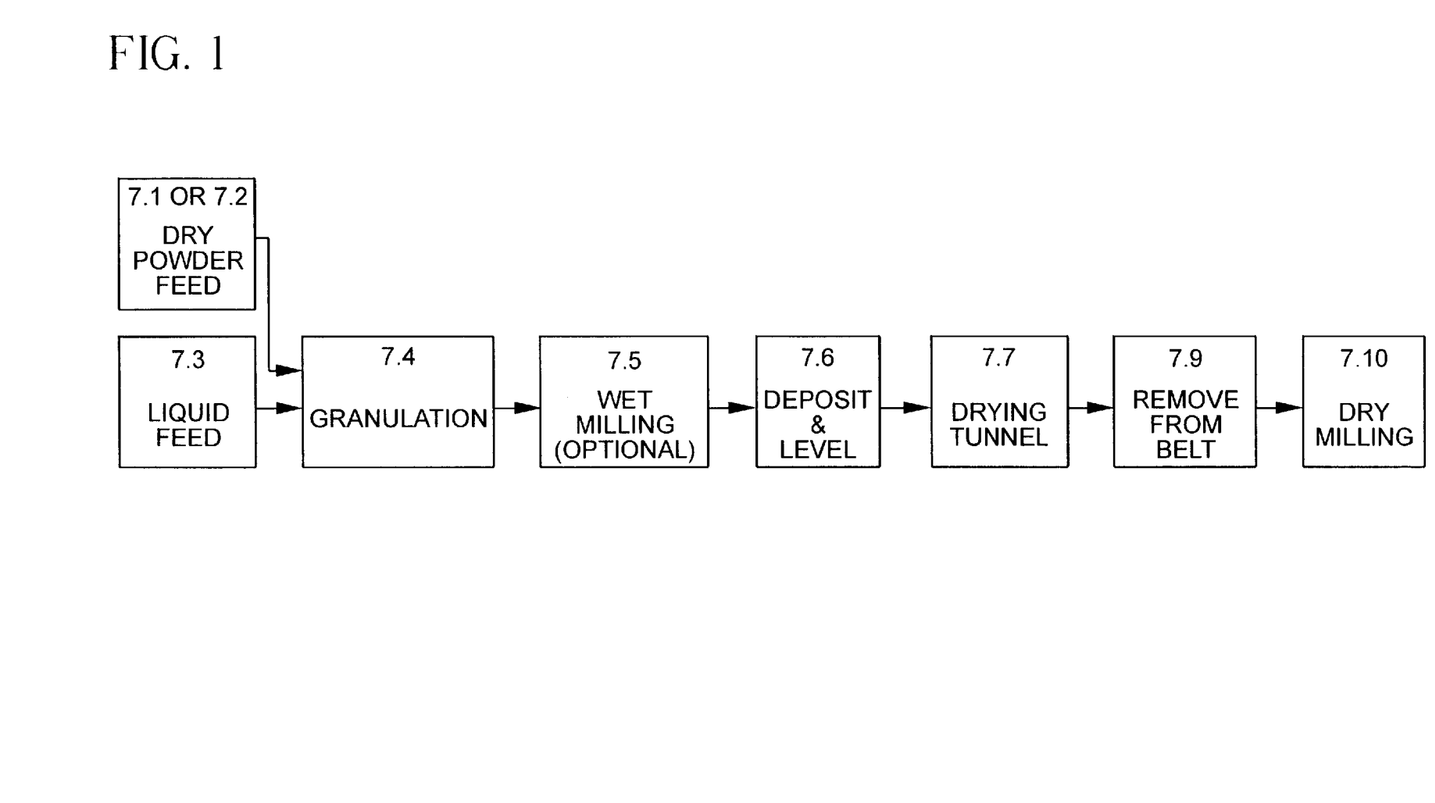
FIG. 1 is a schematic block diagram of the process and apparatus according to the present invention.

As shown schematically in FIG. 1, this system comprises a twin screw wet granulator-chopper (TSWGC) having two or more screws rotating in the same or opposite directions for the granulation stage 7.4. To the TSWGC, one or more solid and/or liquid materials are fed, typically including at least one pharmaceutically active ingredient, at feed stages 7.1–7.3. The active ingredient(s) combined with excipients, water, and possibly other additives, are continuously introduced at one or more points along the length of the TSWGC.

In the TSWGC 1, as shown in FIGS. 2, 3A, 3B, and 4, the solid ingredients are fed through one or more side or top powder feeders 2 and liquid ingredients are fed through a top or bottom feeder 4, all near the upstream end of the TSWGC 1. The liquid ingredients are injected into the TSWGC 1 by a pump 3 connected to a fluid reservoir 5. The liquid and solid ingredients are mixed into a relatively homogeneous wet mixture as they travel along the length of the TSWGC 1.

Figure 3A:
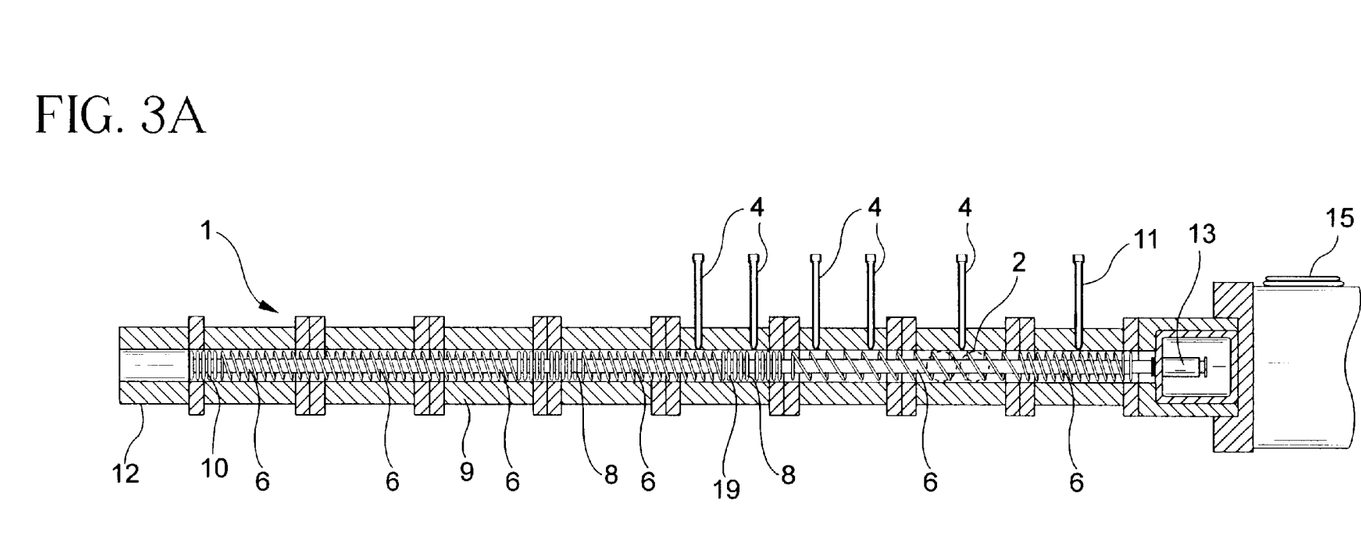
FIG. 3A is one embodiment of the twin screw granulator-chopper according to the present invention.
Figure 3B:
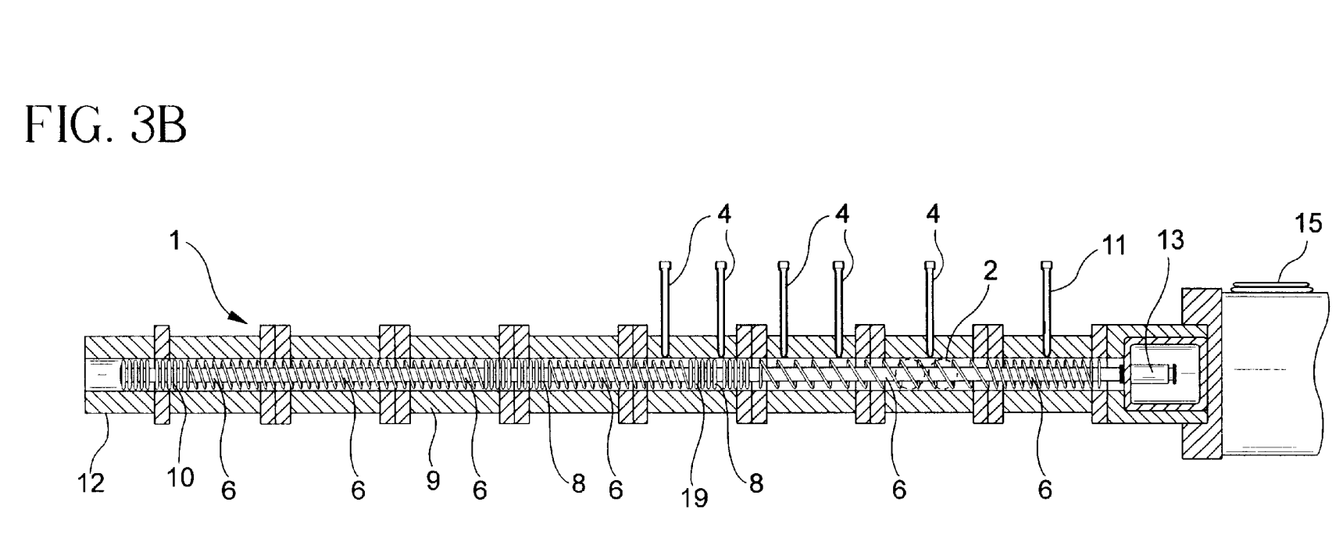
FIG. 3B is another embodiment of the twin screw granulator-chopper according to the present invention.

More specifically, as shown in FIGS. 3A and 3B, a typical arrangement of the twin screw elements used in the TSWGC 1 of the present invention comprises a housing 9 containing conveying elements 6, mixing (granulating) elements 8, and chopping elements 10 which achieve distributive and, when desired, dispersive mixing. These elements produce a homogeneous granulation with the required densification to enhance the ease of further processing in making the desired solid oral dosage form. The TSWGC 1 of the present invention is capable of processing active ingredients and additives with varying bulk densities to produce a homogeneous granulation.

The TSWGC of the present invention is characterized based on the diameter of its screw elements. For example a TSWGC with a screw diameter of 18 mm is referred to as an 18 mm TSWGC. The screw diameter is generally between about 16 mm and about 135 mm. The length of individual barrels (housing) 9, i.e., the length of the entire granulating zone, is designed to be a multiple of the screw diameter. Generally, the ratio of the length of the housing to the screw diameter is between about 20:1 and about 60:1. Nevertheless, this ratio may be altered to accommodate any specific requirements of the granulating process.

The length of the individual elements in the housing is generally in multiples of 15 mm. The pitch of the conveying element 6 is generally between about 15 mm and about 180 mm depending on the size of the machine and the requirements for the particular granulating process. For example, for a 50 mm screw, the pitch of the conveying elements is generally between about 20 mm and about 72 mm.

For mixing and chopping functions, several different designs can be used, including but not limited to kneading discs, combing mixers, gear mixers, pin mixers, and calender gap mixers, depending on the ingredients being granulated. In addition, the conveying and mixing elements 6 and 8 may include short lengths of reverse threads, kneading elements, and/or gear elements 8 to enhance the mixing process.

In one embodiment of the invention, as shown in FIGS. 3A and 3B, combing choppers 8 and 10 are used for mixing and chopping in a TSWGC 1 with a 34 mm or 27 mm screw diameter having a housing length/screw diameter ratio of 28:1. In each combing mixer 8, there are five rows of vanes 19 with eight passages within each row. The vanes 19 are protrusions from a ring-like structure with gaps in between each vane 19. The gaps between adjacent rows of vanes are alternating so that there are gaps between the rows which facilitate mixing of the granulation. In one embodiment, the vanes are at a pitch angle of 120° toward the output end of the TSWGC which allows the granulation to be pushed through the TSWGC. A flat pitch or other pitch angles can also be used depending on the ingredients being granulated.

The screw sizes, threads, pitches, and angles of contact with the housing 9 and granulation may vary depending on the active ingredient(s) and excipients being mixed into a granulation product and the extent of production. In any case, conventionally used extruder screws may be incorporated into the TSWGC.

The chopping element 10 shown in FIGS. 3A and 3B are positioned at the terminal end 12 of the TSWGC 1 to eliminate lumps in the granulation and to maintain the structure of the granulation. Additionally, the shaft length may be extended so that the chopping element 10 at the terminal end 12 may be flush with the open end of the barrel or extend further out (as shown in FIG. 3B) by an additional 1 to 60 mm, preferably about 1 to 30 mm, to further assist in maintaining the formation of discrete granules. Also, the TSWGC 1 contains an optional guard device and chute 12, FIGS. 3A and 3B, to assist in maintaining the path of the wet granulation for further processing and an optional discharge bin 17 for receiving discarded waste materials.

As shown in the exemplary TSWGC's 1 of FIGS. 3A and 3B, the TSWGC 1 includes a relief vent 11; a retention seal 13 and a combination drive motor and gear reducing elements 15 for rotating the twin screws. Unlike conventional twin screw extruders, the TWSGC of the present invention does not include a die at its outlet end. Rather, housing 19 is open at the outlet end of the twin screw extruders, and granulated product exits therefrom freely.

In general, wet granulation stage 7.4 in the TSWGC operates at room temperature, although the temperature may be raised, to increase the solubility of poorly soluble active ingredients, for controlled release purposes, to assist in the drying process, or for any other reason to affect product characteristics. Temperature within the TSWGC may be maintained by a heat exchange fluid, circulated in a jacket surrounding the housing 9 of the TSWGC 1, although electric heating may also be used.

The wet granulation process variables, such as the extruder barrel temperature profile, screw speed, screw design, and rate of adding different mix components are controlled in response to various downstream requirements (variables), such as the granulation bulk density, moisture level, uniformity of distribution of active ingredient(s), product solubility, degree of mixing, temperature, and product material inventory at any stage following mixing, granulation, and chopping. Specifically, dried granulation moisture and the uniformity of distribution of active ingredient(s) are monitored on-line for optimal product composition. In addition, the control system may include alarm or warning signals to indicate various processing parameters or events, such as an error condition system overload or unacceptable product characteristics.

Upon exiting the TSWGC, the wet granulation is deposited and leveled (stage 7.6 in FIG. 1) to the appropriate height and thickness on the drying belt by a load/leveling device. The granulation is then transported by the load/leveling device into a drying stage (7.7 in FIG. 1) to undergo drying preferably induced by dielectric energy, such as radio frequency (RF) or microwave energy. Optionally, the wet granulation may be further processed in a wet mill (Stage 7.5 in FIG. 1) before being conveyed to the dryer. The granulation may also be dried by other processes and apparatus, such as paddle, fluid bed, or infrared drying with or without the application of a vacuum.

Figure 5:
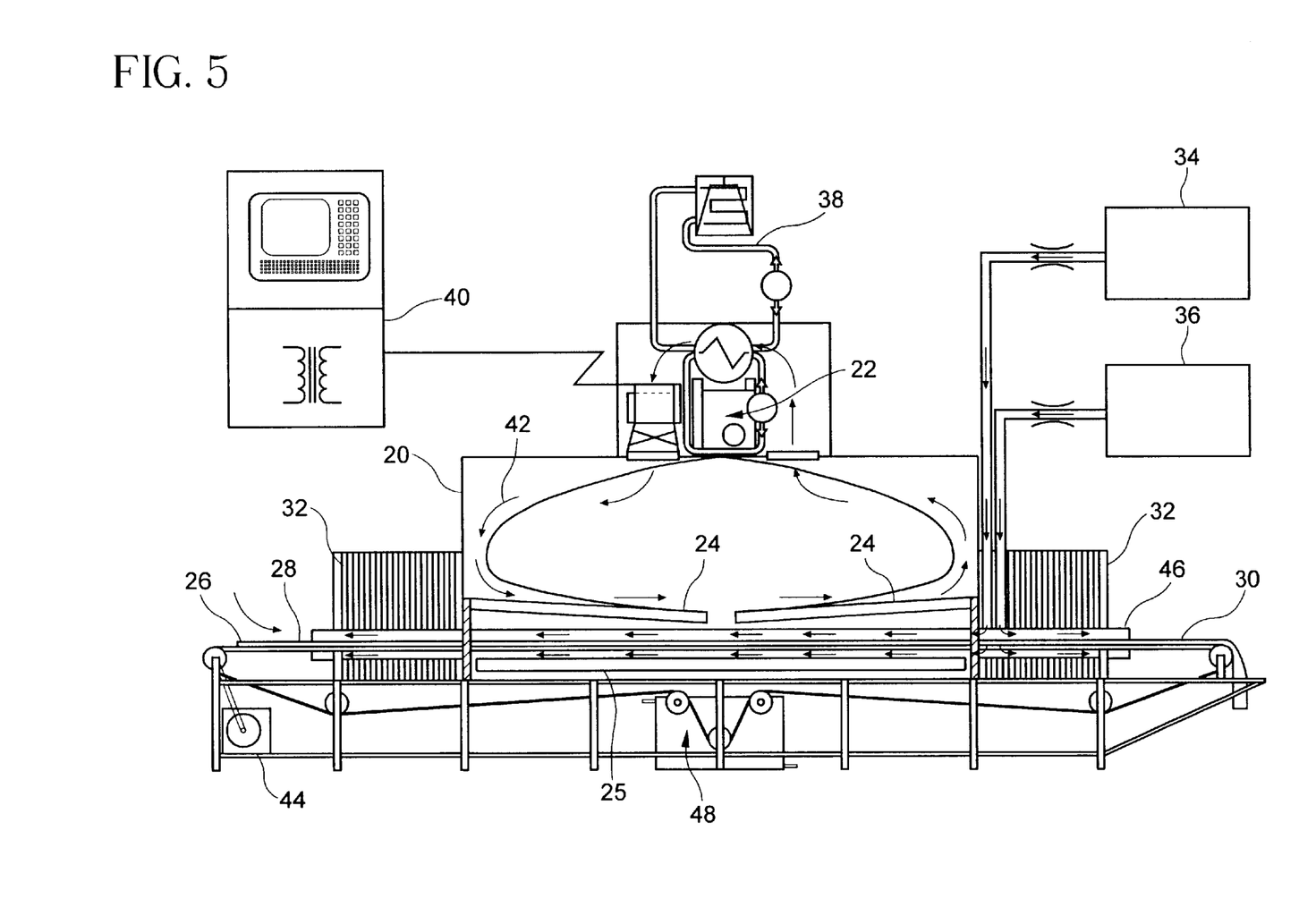
FIG. 5 is a schematic representation of the drying apparatus according to the present invention.
Figure 6:
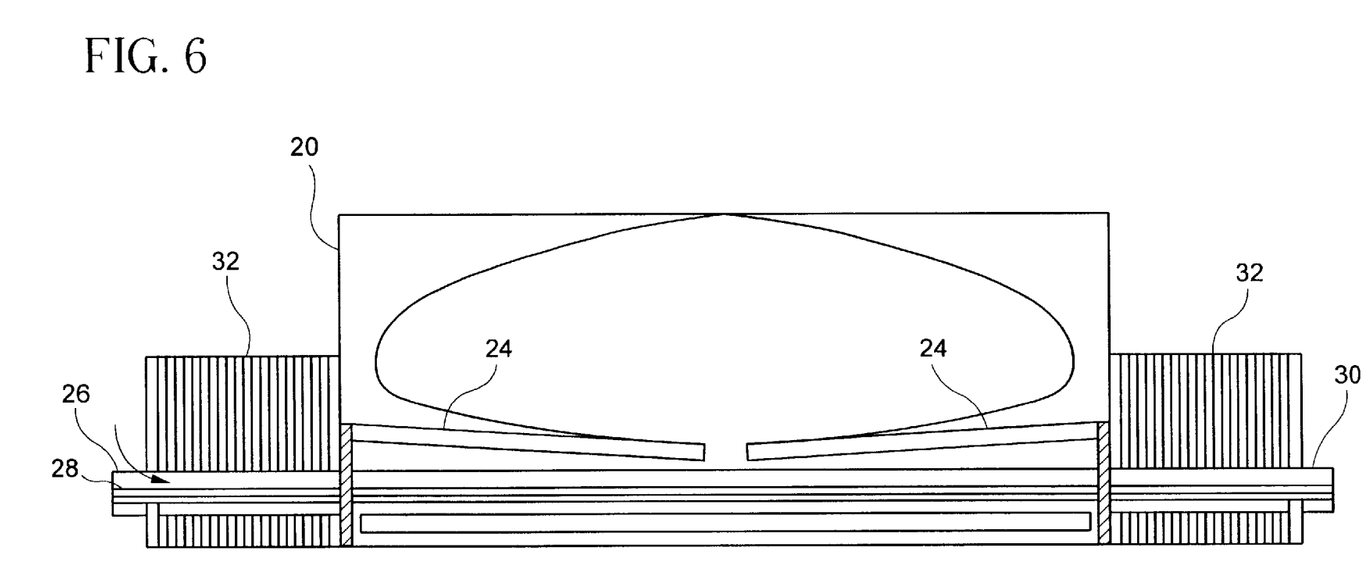
FIG. 6 is a schematic representation of an electrode configuration useful in the drying apparatus according to the present invention.

The drying Stage 7.7 may comprise, as illustrated in FIGS. 5 and 6, an RF generator 22 which creates an alternating electric field between the two electrodes 24. For RF sources, based on international ISM (Industrial, Scientific, Medical) standards, the frequencies used are 27.12 MHz and 40.56 MHz. The frequencies used for microwave dryers are 915 MHz and 2450 MHz for low frequency, and several gigahertz in case of milimeter wave, for high frequency. The material to be dried is conveyed between the electrodes. The design enables a single pass, continuous, drying system.

The dried granulation is removed from the drying belt and conveyed (Stage 7.9 in FIG. 1) into an on-line mill, such as a cone mill, via another device/conveying mechanism, for milling (Stage 7.10 in FIG. 1) the granulation into the sizes typically used in pharmaceutical dosage forms. Depending on the reactivity of the product material, this may be done under nitrogen or other inert gas atmosphere. After exiting the dry mill, the milled granulation is optionally blended with other commonly used excipients prior to being compressed into tablets or filled into hard gelatin capsules.

As shown in FIGS. 5 and 6, the drying apparatus 20, which uses radio frequency (RF) energy, incorporates an RF generator 22 which creates an alternating electric field between two electrodes 24 positioned on opposite sides of the apparatus 20. The material to be dried enters the drying apparatus 20 at its input end 26 and is conveyed by a drying belt 28, powered by a drive motor 44. A load/leveler device levels the wet granulated material on the drying belt 28 at the required height. The leveler device forms a bed of granulated material that travels along the belt 28 through the drying zone at a predetermined speed. The belt 28 can be continuously cleaned by a belt cleaning mechanism 48.

As the granulation enters the portion of the drying apparatus 20 containing the electrodes 24, the material to be dried is acted upon by the alternating electric field created by the electrodes 24 which heats the material. An optional inner tunnel 46 may be inserted to further isolate the product without impeding the distribution of RF energy. Electrodes 24 along with ground electrode 25 are used to produce the electric field. The electrodes 24 are arranged in a specific manner to allow for controlled heating of the granulation bed. Different electrode configurations such as parallel plate (as shown in FIG. 5), staggered rod, etc. may be used. The number of electrodes may be increased depending on the energy requirements for drying particular materials.

The friction caused by constant reorientation of water molecules under the influence of the alternating electric field between the electrodes 24 causes the water in the material to rapidly heat and evaporate. Water vapor is removed from the top and/or bottom of the surface of belt 28 by process air that flows in a co-current (same direction) or counter current (opposite direction) direction as the granulation product is conveyed on the belt. This process air flow is caused by conveying heated 34 and cooled 36 streams of conditioned air. A cooling system 38, with regulator 40, regulates the temperature of the RF generator 22 by regulating the temperature of a circulating stream 42 flowing around RF generator 22. Controller 40 may also control other parameters and other conditions to optimize drying of the granulated product. Attenuators 32 at both the input 26 and output ends 30 prevent radiation leakage from the tunnel 20.

Thus, as the material to be dried (the granulation bed) moves through the drying apparatus/tunnel, the moisture level of the material gradually decreases. The material is maintained in a relatively narrow temperature range to maximize moisture removal.

During drying, the bed can be maintained at a temperature range determined by the nature of the product, usually within about a 30° range, such as from about 75° C. to about 105° C. Nevertheless, using RF energy, it is possible in principle to achieve the required moisture removal at temperatures as low as room temperature. If tolerated by the active ingredient(s) and excipients being granulated, temperatures above 105° C. may also be used. Typical residence times in the tunnel vary from several minutes to a few hours, depending on the required inlet/outlet moisture levels, the properties of the product, and the required product output.

The amount of heat generated in the RF drying apparatus is determined by the frequency of the dielectric energy, the square of the voltage applied across the electrodes, the dimensions of the material being dried, and the dielectric loss factor of the material being dried (this represents the ease with which the material can be heated by this method). Dielectric heating is volumetric in nature. Given its polar nature, water is selectively and volumetrically heated when placed in the drying apparatus of the present invention. The selective and volumetric heating increases the rate of heat transfer compared to that of conventional heating/drying systems and reduces the residence time in the drying apparatus, which is preferable to protect materials that may degrade at elevated temperatures. The selective heating of water and in situ evaporation of moisture largely eliminates temperature and moisture variations in the dried material and, thus, can improve product quality and/or further processing of the dried material.

The use of dielectric energy, i.e., RF or microwave energy, for drying obviates the need to convey the material to be dried through the drying zone more than once for sufficient drying of the material.

The dried material is conveyed out of drying apparatus 20 by belt 28 through output end 30 of drying apparatus 20. From drying apparatus 20, the dried material is conveyed and further processed by a milling device to particle sizes suitable for compression into a tablet or incorporation into a hard gelatin capsule or sachet.

Any suitable active ingredient that can be formulated into a solid dosage form can be used in the process, apparatus, and system of the present invention. Examples of the therapeutic indications and specific active ingredients are listed below.

1. Antipyretic, analgesic, and anti-inflammatory agents, such as indomethacin, aspirin, diclofenac sodium, ketoprofen, ibuprofen, mefenamic acid, dexamethasone, hydrocortisone, prednisolone, acetaminophen, phenylbutazone, flufenamic acid, sodium salicylate, tramadol hydrochloride tablets, oxaprozin, and etodolac.

2. Antiulcer agents, such as omeprazole, cimetidine, lansoprazole, nizatidine capsules USP, ranitidine hydrochloride, famotidine, and nizatidine.

3. Coronary vasodilators, such as nifedipine, isosorbide dinitrate, diltiazem hydrochloride, dipyridamole, isosorbide monotrate, verapamil, nicardipinenifedipine, and nitroglycerin tablets.

4. Peripheral vasodilators, such as sildenafil citrate, cinepazide maleate, cyclandelate, and pentoxiphylline.

5. Antibiotics, such as ampicillin, amoxicillin, cefalexin, clarithromycin tablets, cefuroxime axetil tablets, cefropzil, erythromycin ethyl succinate, bacampicillin hydrochloride, minocycline hydro-chloride, chloramphenicol, tetracycline, and erythromycin.

6. Synthetic antimicrobial agents, such as nalidixic acid, enoxacin, cinoxacin, levofloxacin tablets, ofloxacin, norfloxacin, ciprofloxacin hydrochloride, and sulfamethoxazole-trimethoprim.

7. Antispasmodic agents, such as propantheline bromide, atropine sulfate, and scopolamine.

8. Antitussive and antiasthmatic agents, such as theophylline, aminophylline, codeine phosphate, dextromethorphan hydrobromide ephedrine hydro-chloride, and noscapine.

9. Bronchodilators, such as salbutamol sulfate, pir-buterol hydrochloride, bitolterol mesilate, clenbuterol hydrochloride, terbutaline sulfate, mabuterol hydrochloride, fenoterol hydrobromide, and methoxyphenamine hydrochloride.

10. Diuretics, such as furosemide, acetazolamide, trichlormethiazide, cyclothiazide, hydrochlorothiazide, hydroflumethiazide, spironolactone, and triamterene.

11. Muscle relaxants, such as tolperisone hydrochloride, eperisone hydrochloride, tizanidine hydrochloride, mephenesin, chlorzoxazone, phenprobamate, methocarbamolbaclofen, and dantrolene sodium.

12. Cerebral metabolism improving agents, such as meclofenoxate hydrochloride.

13. Tranquilizers, such as oxazolam, diazepam temazepam, meprobamate, nitrazepam, and chlordiazepoxide, sulpiride, clocapramine hydrochloride, zotepine, chloropromazine, and haloperidol.

14. Beta-Blockers, such as pindolol, propranolol hydrochloride, metoprolol tartrate, labetalol hydrochloride, oxprenolol hydrochloride, acebutolol hydrochloride, metoprolol succinate, bufetolol hydrochloride, alprenolol hydrochloride, and nadolol.

15. Antiarrhythmic agents, such as procainamide hydrochloride, disopyramide, quinidine sulfate, propafenone hydrochloride, and mexiletine hydrochloride.

16. Antigout agents, such as allopurinol, probenecid, colchicine, warfarin sodium tablets USP, and sulfinpyrazone.

17. Anticoagulants, such as ticlopidine hydrochloride, dicoumarol, and warfarin potassium.

18. Antiepileptics, such as gabapentin capsules, gaphenytoin, divalproex sodium, sodium valproate, and metharbital.

19. Antihistaminics, such as loratadine, cetirizine hydrochloride, chlorpheniramine maleate, fexofenade hydrochloride, clemastine fumarate, and cyproheptadine hydrochloride.

20. Antiemetics, such as difenidol hydrochloride, metoclopramide, and trimebutine maleate.

21. Antihypertensive agents, such methyldopa, prazosin hydrochloride, bunazosin hydrochloride, clonidine hydrochloride, budralazine bisporolol fumarate and hydrochlorothiazide, terazosin hydrochloride, and urapidil.

22. Sympathomimetic agents, such as dihydroergotamine mesilate, isoproterenol hydrochloride, and etilefrine hydrochloride.

23. Expectorants, such as bromhexine hydrochloride, carbocysteine, and cysteine methyl ester hydrochloride.

24. Oral antidiabetic agents, such as glibenclamide, glimepiride tablets, glipizide, metformin hydrochloride tablets, troglitazone, tolbutamide, and glymidine sodium.

25. Iron preparations, such as ferrous sulfate and dried iron sulfate.

26. Vitamins, such as vitamin $B_{12}$, vitamin $B_6$, vitamin C, and folic acid.

27. Therapeutic agents for pollakiuria, such as flavoxate hydrochloride, oxybutynin hydrochloride, and terodiline hydrochloride.

28. Angiotension converting enzyme inhibitors, such as enalapril maleate, enalaprilat USP, fosinopril sodium tablets, alacepril, lisinopril, quinapril hydrochloride tablets, ramipril, and delapril hydrochloride.

29. Other types of active ingredients, such as acetohexamide, ajamaline, alendronate sodium, amlodipine besylate, amylobarbitone, atorvastin calcium, bendrofluozide, benzbromarone, benzonatate, benzylbenzoate, betametharzone, brand of paroxetine hydrochloride, bupropion hydrochloride, buspirone HCl USP, chloramphenicol, chlorpropamide, chlorthalidone, clofibrate, conjugated estrogens tablets USP, corticsoteroids, diazepam, dicumerol, digitoxin, digoxin, dihydroxypropyltheophylline, diltiazem HCl, doxazosin mesylate, ergot alkaloids, ethotoin, felodipine, fluoxetine hydrochloride, fluconazole, fluvastatin sodium, frusemide, glutethimide, griseofulvin, hydrochlorothiazide, hydrocortisone, hydroflumethiazide, hydroquinone, hydroxyalkylxanthines, indomethacin, isoxsuprine hydrochloride, ketoprofen, khellin, levothyroxine sodium USP, losartan potassium tablets, lovastatin USP, meprobamate, nabilone, nefazodone hydrochloride, nicotainamide, nifedipine, nitrofurantoin, novalgin, nystatin, papaverine, paracetamol, phenylbutazone, phenobarbitone, pravastin sodium, prednisolone, prednisone, primadonel reserpine, risperidone, romglizone, salicylic acid, salmeterol xinafoate, sertraline hydrochloride, simvastatin, spiranolactone, sulphabenzamide, sulphadiamadine, sulphamethoxydiazine, sulphamerazine, succinylsulphathiazole, sulphamethizole, sulphamethoxazole, sulphathiazole, sulphisoxazole, sumatriptan succinate, testosterone, tolazoline, tolbutamide, trifluopera-zine, trimethaprim, valsartan capsules, zolpidem tartrate, and other water insoluble active ingredients.

The excipients (polymers, small molecules, and organic and inorganic compounds) which may be used in the present invention can be any natural or synthetic substance that can be used as a raw material in the manufacture of pharmaceutical products. Examples of excipients include: hydroxypropylmethylcellulose phthalate, hydroxypropylmethylcellulose acetate succinate (AQOAT), carboxymethylethylcellulose, cellulose acetate phthalate, Eudragit acrylic copolymers, methacrylic copolymer LD, methacrylic copolymer S, aminoalkyl methacrylate copolymer E, poly(vinyl acetal) diethylaminoacetate, polyvinylpyrrolidone, ethylcellulose, methacrylic copolymer RS, polyvinyl alcohol, high molecular weight polyethylene glycols, methylcellulose, hydroxypropylcellulose, hydroxypropylmethylcellulose, carboxymethylcellulose sodium, dextrin, pullulan, Aca-cia, tragacanth, sodium alginate, propylene glycol alginate, agar powder, gelatin, starch, processed starch, phospholipids (such as lecithin), glucomannan, cetanol, medium chain triglycerides, polyoxyethylene-polyoxypropylene glycol (Pluronic), macrogols (200, 300, 400, 600, 1000, 1500, 1540, 4000, 6000, 20000), polyethylene glycols, such as PEG 200, PEG 300, PEG 400, and PEG 600, triacetin, and triethyl citrate (Citroflex), Tweens 20, 60, and 80, Span 20, Span 40, Pluronics, polyoxyethylene sorbitol esters, monoglycerides, polyoxyethylene acids, polyoxyethylene alcohols and mixtures thereof, calcium carbonate, dibasic calcium phosphate dihydrate, calcium sulfate, microcrystalline cellulose, lactose, magnesium carbonate, magnesium oxide, maltodextrim, mannitol, starch, sucrose, compressible sugar, croscarmellose, crospovidone, hydroxyl propyl cellulose, Hydroxypropyl methylcellulose, Sodium starch glycolate, Pregelatinized starch, Gelatin, Guar gum, Povidone, Alginic acid, Ascorbic acid, Citric acid, Cycludextrim, Dextrates, Lecithin and other fatty acids, Colloidal silicon dioxide, Sodium benzoate, Sodium bicarbonate, and Talc.

The excipients can be used independently or, if necessary, in a combination of two or more types of excipients. The processing parameters, such as pressure, temperature, feed rate of material, amounts and feed rates of water and other excipients used in the production process of the present invention are dependent on the type of active ingredient and excipients, among other conditions. Moreover, the combination of operating parameters of the system must be set such that the active ingredient and excipients will be maintained at temperatures below their decomposition points and the desired characteristics of the pharmaceutical product will be achieved.

Figure 2:
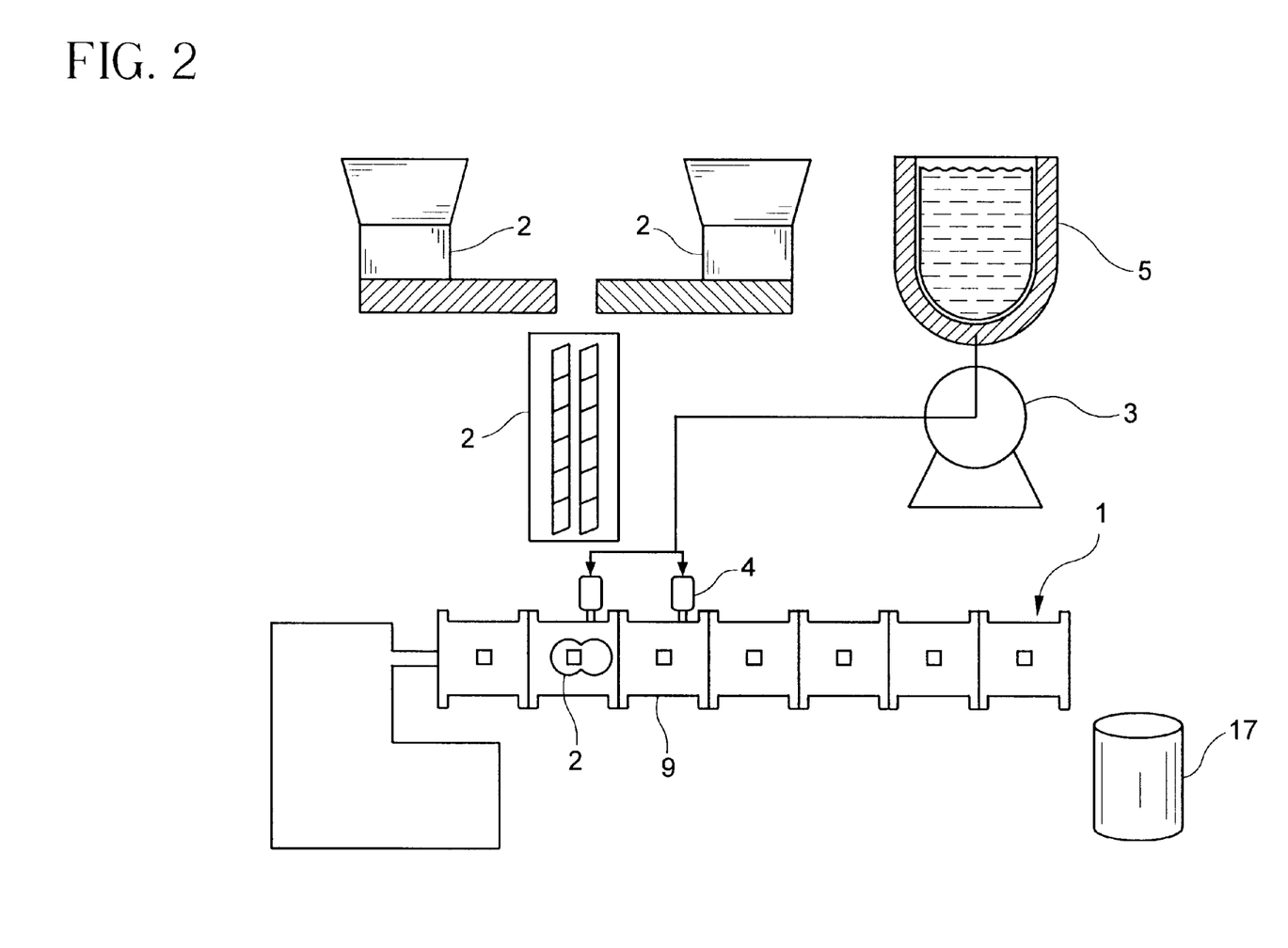
FIG. 2 is schematic representation of a twin screw wet granulator-chopper according to the present invention.

Certain aspects of the present invention are illustrated by the examples, which follow. In the examples below, continuous wet granulation, drying, and milling were evaluated by producing a tablet containing an investigational drug product utilizing the TSWGC of the present invention, specifically, a co-rotating TSWGC, as shown in FIG. 2. In Example 2, the granulation produced by the TSWGC was dried in a drying apparatus/tunnel using dielectric energy, specifically, radio frequency energy (as shown in FIGS. 5 and 6) (the granulation produced in Example 1 was dried by a conventional method). The examples are meant by way of illustration only and do not serve to limit the scope of the present invention.

EXAMPLE 1

Production of Investigational 300 mg Tablet

A pre-blend of an investigational drug and excipients was prepared by mixing the weighed ingredients, in a 16 qt V-blender. The blend of dry ingredients was fed from a loss-in-weight solid feeder into the TSWGC configured with a side stuffer mechanism. The feeder was adjusted to yield a feed rate of 11.4 kg/hour. An aqueous solution containing a surfactant was used as a granulating fluid and injected into the TSWGC using a piston pump at a rate of 8.64 kg/hour. A total of 6.8 liters of the fluid were used for this product. The temperature of the TSWGC was maintained at 26° C. and the screw speed was 177 rpm at a maximum torque of 19%.

The granulation was prepared by the TSWGC with an output of 18.2 kg/hour. The granulation was dried in a tray dryer at 50° C. for 9 hours from a moisture level of 13.6% to a moisture level of 1.0%.

The dried granulation was milled in a hammer mill and the final blend of product was prepared by mixing the milled granulate product with the listed external excipients in a V-blender. The fillers and disintegrant were added to the milled granulation product and blended for 10 minutes at 20 rpm. Then, lubricant was added to the resulting product and blended for another 5 minutes at 20 rpm.

Tableting was performed using a six station tablet press. The final blend was compressed using standard concave oval tooling, having the dimensions 0.645"×0.3295"×0.0465," at a press speed of 30 rpm. A compression profile (as shown in Table 1) was generated by compressing the blend over a range of applied forces.

The results of physical testing on the investigational drug formulation, are also outlined in Table 1: (1) the formulation exhibited good compressibility and disintegration with the tablet cores disintegrating within 6 minutes; and (2) the dissolution testing results (not shown in Table 1) indicated complete release of investigational drug within 20 minutes from all individual tablets.

TABLE 1

Investigational Drug Tablets-Physical Testing

| Compression Force (Kn/kg)$^{(3)}$ | Hardness (kPa) (n = 10) | Disintegration (minutes) (n = 3) | Friability (%) (n = 20) Time = 10 Minutes |
|---|---|---|---|
| 5.16/526.3 | 9.1 ± 0.5 | 2.0 | 0.88 |
| 7.17/731.3 | 14.2 ± 0.8 | 3.0 | 0.35 |
| 8.07/823.1 | 16.3 ± 0.9 | 3.7 | 0.32 |
| 9.27/945.5 | 19.3 ± 1.3 | 4.7 | 0.18 |
| 11.77/1200.5 | 24.2 ± 1.4 | 5.3 | 0.18 |

EXAMPLE 2

Production of Investigational 600 mg Tablet (Higher Strength)

Figure 4:
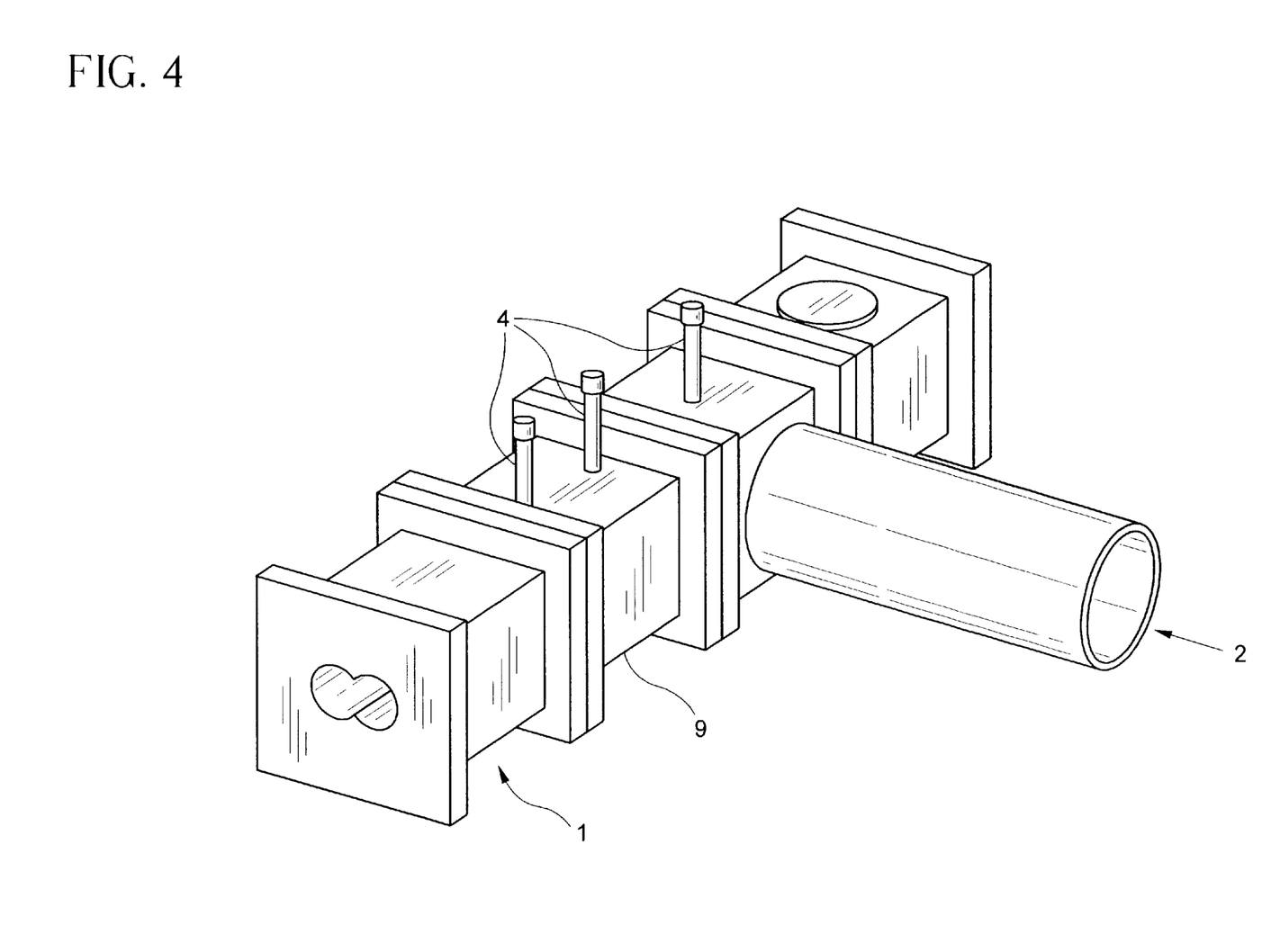
FIG. 4 is an isometric view of the feeder system of the twin screw granulator-chopper according to the present invention.

A pre-blend of an investigational drug, at a higher strength than in Example 1, and excipients was prepared by mixing the weighed ingredients for 20 minutes at 25 rpm in a 42 liter bin blender. The powder blend was then introduced into the TSWGC according to the present invention by a side stuffer feed mechanism (as shown in FIGS. 2–4). Three pairs of mixing elements in combination with different sized conveying elements were used.

The dry ingredients were fed from a loss-in-weight solid feeder configured with a side stuffer mechanism connected to a hopper containing the solid ingredients. A vertical agitator was used to mix the contents of the hopper. The feed rate of the powder feed was 10.5 kg/hour. An aqueous solution containing a surfactant was used as a granulating fluid and injected into the TSWGC using a piston pump at a rate of 3.2 kg/hour. A total of 2.5 liters of the fluid were used for this product. The temperature of the TSWGC was maintained at 26° C. and the screw speed was 200 rpm at a maximum torque of 35%. The granulation was prepared by the TSWGC with an output of 14.5–15.1 kg/hour. The granulation was dried in a drying tunnel using radio frequency energy from a moisture level of 22.9% to a moisture level of less than 2.0%. The granulation was laid down on a 24 inch wide belt. The granulation bed was 22 inches wide and 1 inch deep and the belt speed was 0.26 feet/minute.

The dried granulation was milled in a hammer mill and the final blend of product was prepared by mixing the milled granulate product and external excipients in a V-blender. The fillers and disintegrant were added to the milled granulation product and blended for 10 minutes at 20 rpm. Then, lubricant was added to the resulting product and blended for another 5 minutes at 20 rpm.

Tableting was performed using a six station tablet press. The final blend was compressed using standard concave oval tooling, having the dimensions 0.7"×0.355"×0.07," at a press speed of 30 rpm. A compression profile was generated by compressing the blend over a range of applied forces.

The results of physical testing on the high strength investigational drug formulation are outlined in Table 2: (1) the formulation exhibited good compressibility and disintegration with the tablet cores disintegrating within seven minutes; and (2) the dissolution testing results indicate complete release of drug within 20 minutes from tablets compressed over the entire hardness range.

TABLE 2

High Strength Investigational Drug Tablets-Physical Testing

| Compression Force (kN/kg)$^{(3)}$ | Hardness (kp) (n = 10) | Disintegration (min) (n = 3) | Friability (%) (n = 20) Time = 10 Minutes |
|---|---|---|---|
| 4.66/475.5 | 8.5 ± 0.9 | 4.2 | 2.76 |
| 6.03/614.7 | 12.0 ± 0.9 | 5.5 | 1.38 |
| 6.58/671.0 | 13.7 ± 1.1 | 5.3 | 0.82 |
| 8.54/870.8 | 18.9 ± 1.2 | 6.0 | 0.39 |
| 9.93/1012.5 | 22.3 ± 1.7 | 6.9 | 0.49 |

While this invention has been described with respect to specific embodiments thereof, it is not limited thereto. In its most general sense, this invention encompasses a twin screw granulator-chopper and/or radio frequency or microwave dryer used to produce a pharmaceutical granulation, and a single pass, continuous system for producing such products incorporating the granulator-chopper, the dryer, or both. Nor is the present invention limited to the examples shown. Rather, various modifications may be made in the details of the invention and its various embodiments as described and exemplified without departing from the true spirit and scope of the invention. The claims which follow should be construed accordingly.

What is claimed:

1. A single pass continuous processing system for producing pharmaceutical granulation, comprising:

(a) powder and liquid feeders to feed at least one pharmaceutically active ingredient and additives;

(b) a twin screw wet granulator-chopper device for granulating the active ingredient and additives received from the powder and liquid feeders into a wet granular product said twin screw wet granulator-chopper including a housing surrounding said device, said housing including a non-extruding opening at the outlet thereof;

(c) conveying, loading, and leveling means for conveying the wet granulation from the outlet of said twin screw wet granulator-chopper, loading the wet granulation on a dryer belt, and leveling the wet granulation to a desired height;

(d) a drying apparatus for receiving the wet granulation from the dryer belt and drying the wet granulation using dielectric energy;

(e) conveying means for transporting the dried granulation from the drying apparatus for size reduction;

(f) a mill for reducing the dried granulation to particles of a desired size; and (g) control means for controlling process variables of at least one of the powder and liquid feeders, the twin screw wet granulator-chopper, the conveying, loading, and leveling means, the drying apparatus, the conveying means, and the mill to optimize production of pharmaceutical granulation.

2. The system of claim 1 wherein the powder is fed through a side stuffer unit and the liquid is fed into a liquid injector for addition into the twin screw wet granulator-chopper.

3. The system of claim 1 wherein the twin screw wet granulator-chopper comprises a mechanism for chopping the granulation into discrete particles.

4. The system of claim 1 wherein the control means includes means for monitoring conditions of the system and controlling process variables of at least one of the powder and liquid feeders, the twin screw wet granulator-chopper, the conveying, loading, and leveling means, the drying apparatus, the conveying means, and the mill.

5. The system of claim 4 wherein the moisture content of the granulation is monitored on-line and the liquid feeder is controlled to adjust the moisture content.

6. The system of claim 4 wherein the uniformity of distribution of the active ingredient is monitored on-line and at least one of the powder and liquid feeders, the twin screw wet granulator-chopper, the conveying, loading, and leveling means, the drying apparatus, the conveying means, and the mill is controlled to adjust the uniformity of distribution.

7. The system of claim 1 wherein the twin screw wet granulator-chopper comprises two or more screws having interengaging threads adapted to rotate in the same or opposite directions and granulate the active ingredient and additives.

* * * * *

UNITED STATES PATENT AND TRADEMARK OFFICE
Certificate

Patent No. 6,499,984 B1                                                    Patented: December 31, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Isaac Ghebre-Sellassie, Morris Plains, NJ; Matthew J. Mollan, Jr., Succasunns, NJ; Mayur Lodaya, Succasunna, NJ; Mebrahtu Fessehaie, New York, NY; and Umang Shah, Ann Arbor, MI.

Signed and Sealed this Tenth Day of January 2006.

<div style="text-align:right">

MICHAEL COLAIANNI
*Supervisory Patent Examiner*
Art Unit 1732

</div>